(12) United States Patent
Kwon et al.

(10) Patent No.: US 11,067,581 B2
(45) Date of Patent: Jul. 20, 2021

(54) DETECTION OF CEREBROSPINAL FLUID

(71) Applicants: NEUROLOGICAL SURGERY, P.C., Rockville Centre, NY (US); RENSSELAER POLYTECHNIC INSTITUTE, Troy, NY (US)

(72) Inventors: Seok-Joon Kwon, Niskayuna, NY (US); Robert J. Linhardt, Albany, NY (US); Jonathan S. Dordick, Schenectady, NY (US); William J. Sonstein, Windham, NH (US); Fuming Zhang, Watervliet, NY (US)

(73) Assignees: NSPC TECHNOLOGIES, LLC, Rockville Centre, NY (US); RENSSELAER POLYTECHNIC INSTITUTE, Troy, NY (US)

( * ) Notice: Subject to any disclaimer, the term of this patent is extended or adjusted under 35 U.S.C. 154(b) by 0 days.

(21) Appl. No.: 15/737,352

(22) PCT Filed: Jun. 17, 2016

(86) PCT No.: PCT/US2016/038062
§ 371 (c)(1),
(2) Date: Dec. 18, 2017

(87) PCT Pub. No.: WO2016/205637
PCT Pub. Date: Dec. 22, 2016

(65) Prior Publication Data
US 2019/0004057 A1 Jan. 3, 2019

Related U.S. Application Data

(60) Provisional application No. 62/181,469, filed on Jun. 18, 2015.

(51) Int. Cl.
*G01N 33/543* (2006.01)
*G01N 33/68* (2006.01)
*G01N 33/558* (2006.01)

(52) U.S. Cl.
CPC ....... *G01N 33/68* (2013.01); *G01N 33/54306* (2013.01); *G01N 33/558* (2013.01); *G01N 2333/79* (2013.01)

(58) Field of Classification Search
CPC ............... G01N 33/68; G01N 33/558; G01N 33/54306; G01N 2333/79; G01N 33/543; G01N 2440/32
See application file for complete search history.

(56) References Cited

U.S. PATENT DOCUMENTS

| 2009/0208975 A1* | 8/2009 | D'Costa | B01L 3/5023 435/7.2 |
| 2012/0288959 A1 | 11/2012 | Palmer | |
| 2014/0135235 A1* | 5/2014 | Zhang | C07K 9/00 506/11 |

FOREIGN PATENT DOCUMENTS

| WO | 99/60402 A1 | 11/1999 |
| WO | 00/36418 A1 | 6/2000 |

OTHER PUBLICATIONS

PCT International Search Report and Written Opinion, dated Dec. 5, 2016 in connection with PCT International Application No. PCT/US2016/38062, 15 pages.

(Continued)

*Primary Examiner* — Tracy Vivlemore
*Assistant Examiner* — Nam P Nguyen
(74) *Attorney, Agent, or Firm* — Amster, Rothstein & Ebenstein LLP

(57) ABSTRACT

The invention encompasses methods and test strips for detecting the presence of cerebrospinal fluid (CSF) in a (Continued)

biological sample comprising removing sialo-transferrin and selectively detecting or measuring asialo-transferrin in the biological sample.

11 Claims, 7 Drawing Sheets

(56) References Cited

OTHER PUBLICATIONS

Maria Lonnberg and Jan Carlsson, Membrane Assisted Isoform Immunoassay A Rapid Method for the Separation and Determination of Protein Isoforms in an Integrated Immunoassay, Journal of Immunological Methods 246, accepted Aug. 3, 2000, pp. 25-36, Center for Surface Biotechnology, Uppsala, Sweden and Pharmacia and Upjohn Diagnostics, Uppsala, Sweden.
European Search Report and European Search Opinion dated Nov. 14, 2018 issued in corresponding European Application No. 16812516.9.
Decision to Grant a European Patent Pursuant to Article 97(1) EPC dated Aug. 20, 2020 from European Patent Appln. No. 16812516.9.
Decision to Grant Patent dated Dec. 2, 2020 from Japanese Patent Appln. 2018-517676.

\* cited by examiner

DETECTION OF CEREBROSPINAL FLUID

CROSS-REFERENCE TO RELATED APPLICATIONS

This application is a U.S. national stage entry under 35 U.S.C. § 371 of PCT International Patent Application No. PCT/US2016/038062, filed Jun. 17, 2016, which claims benefit of U.S. Provisional Application No. 62/181,469, filed Jun. 18, 2015, the contents of each of which are incorporated herein by reference into the subject application.

BACKGROUND OF THE INVENTION

Spinal fluid leak as a result of incidental durotomy during spinal surgery is a relatively common complication that occurs with an incidence of 2-17% [1-6]. Usually, spinal fluid leaks are recognized at the time of surgery and are successfully repaired. Occasionally, they present in a delayed fashion, for example, if a small durotomy is not recognized at the time of surgery or if the repair is not ideal initially. Spine surgeons are frequently confronted with post-operative fluid collections that may or may not represent a CSF (cerebrospinal fluid) leak. This is more commonly an issue with lumbar spine surgery for degenerative disease. If a patient presents with positional headaches or with clear fluid leakage, then the diagnosis is more easily made. However, in the post-operative period it is sometimes confounding differentiating seromatous fluid from CSF as a patients' symptoms do not always classically present. A patient may present with a bulging subcutaneous collection of fluid whereupon aspiration, the nature of the fluid is not certain. In surgical decision-making, it would be ideal to confirm the diagnosis of CSF leak quickly so that one can initiate repair, which requires surgical intervention particularly if there is skin drainage, which could result in meningitis. It would be advantageous to know if the collection is a seroma as these can often be treated conservatively without return to the operating room. Currently to distinguish CSF from seromatous fluid, one must send out the fluid sample to a laboratory utilizing electrophoresis and obtaining the results can take three to five days.

A combination of protein separation and detection, using electrophoresis and mass spectrometry, has been successfully applied to identify protein biomarkers in CSF [7]. Transferrin (TF) isoforms among protein biomarkers in CSF have been used as a critical diagnostic marker not only for detecting CSF leakage from liquorrhea but also detecting several diseases, including early stage oral cancer [8], chronic alcoholism [9], and diabetic kidney disease [10].

There remains a need in the art for methods for the rapid detection of CSF leakage.

SUMMARY OF THE INVENTION

The present invention is based on the development of a novel approach to selectively determine CSF β2-transferrin, an asialo-transferrin (aTF) biomarker. Specifically, a method of selectively removing sialo-transferrin (sTF) from serum and other samples has been developed, allowing the detection CSF-derived aTF.

In some embodiments, the invention is directed to a method for detecting the presence of cerebrospinal fluid (CSF) in a biological sample comprising the steps of:
a. obtaining a biological sample;
b. adding an oxidizing agent to the sample in an amount sufficient to generate oxidized sialo-transferrin (sTF), wherein the oxidized sTF comprises an aldehyde group in a terminal residue;
c. contacting the sample obtained from step b with a reagent comprising hydrazide reactive groups wherein the oxidized sTF binds the hydrazide reactive groups to form a complex;
d. removing the complex from the sample to form a residual sample; and
e. detecting the presence of residual transferrin in the residual sample;

wherein the detection of residual transferrin in the biological sample indicates the presence of CSF.

In an additional aspect, the invention is directed to a method for removing sialo-transferrin (sTF) from a biological sample comprising:
a. obtaining a biological sample;
b. adding an oxidizing agent to the sample in an amount sufficient to generate oxidized sTF, wherein the oxidized sTF comprises an aldehyde group in a terminal residue;
c. contacting the sample obtained from step b with a reagent comprising hydrazide reactive groups wherein the oxidized sTF binds the reactive groups to form a complex; and
d. removing the complex from the sample.

In yet additional embodiments, the invention encompasses a method for detecting a CSF leak in a subject during or after surgery comprising:
a. obtaining a first biological sample from the subject prior to surgery and measuring the transferrin present in the first sample; and
b. obtaining a second biological sample from the subject during or after surgery and measuring the transferrin present in the second sample;

wherein a higher amount of transferrin present in the second sample compared to the transferrin present in the first sample indicates a CSF leak.

In further embodiments, the invention is directed to a test strip for detecting or measuring transferrin in a sample comprising:
a. a sample loading region;
b. a filtration region downstream of the sample loading region, wherein the filtration region comprises an immobilized reagent that binds to sTF; and
c. a binding region downstream of the filtration region comprising an anti-transferrin antibody.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows the structure of serum sTF and FIG. 1B shows the structure of CSF sTF and aTF, β2TF.

FIG. 2A shows fluorescent labeling of TF glycoforms sTF and aTF using NHS-rhodamine; FIG. 2B shows the separation of rhodamine-labeled aTF from rhodamine-labeled sTF. FIG. 2C shows the detection limit for rhodamine-labeled TF.

FIG. 3A shows periodate oxidation of terminal sialic acid and capture with SiMAG-Hydrazide. FIG. 3B shows a magnetic separator used to remove captured TF glycoform and recover supernatant.

FIG. 4A shows an agarose gel separation and detection of sTF removed from both CSF and serum. FIG. 4B shows quantification of TF in CSF and serum, respectively before and after single-step periodate oxidation. FIG. 4C shows quantification of residual TF (mainly aTF) in different mixtures of CSF and serum after single-step periodate oxidation. FIG. 4D shows detection of TF after selective removal of sTF from mixture (1:1 v/v ratio) of CSF and various serums (S1: age 29/African male, S2: age 41/Caucasian male, S3: age 61/Hispanic female, S4: age 21/African female).

FIG. 5A shows the removal of sialic acid and oxidation of galactose followed by capture and removal of oxidized sTF. (B), Quantification of two-step enzymatic oxidation for the separation of TF glycoforms.

DETAILED DESCRIPTION OF THE INVENTION

A description of preferred embodiments of the invention follows.

As used herein, the words "a" and "an" are meant to include one or more unless otherwise specified. For example, the term "a particle" encompasses one or more particles.

Figure 1A:
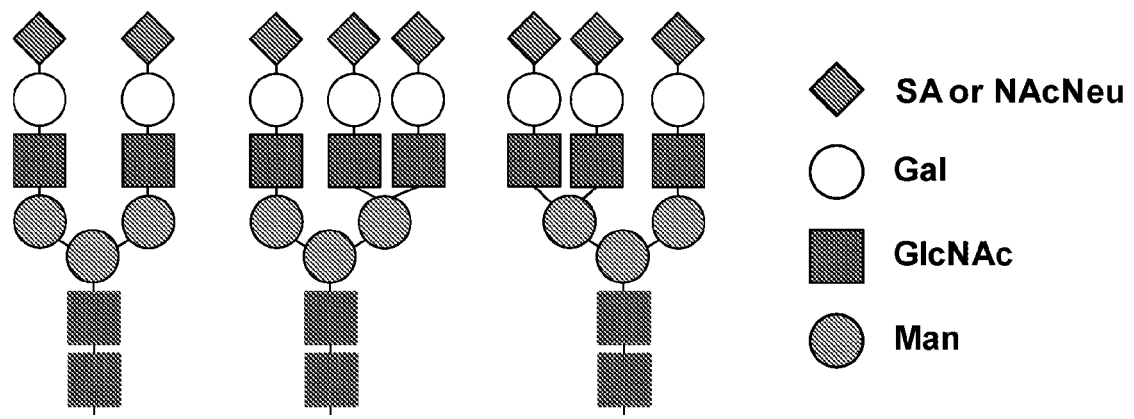
FIGS. 1A and 1B show the structure of glycans present in transferrin glycoforms.
Figure 1B:
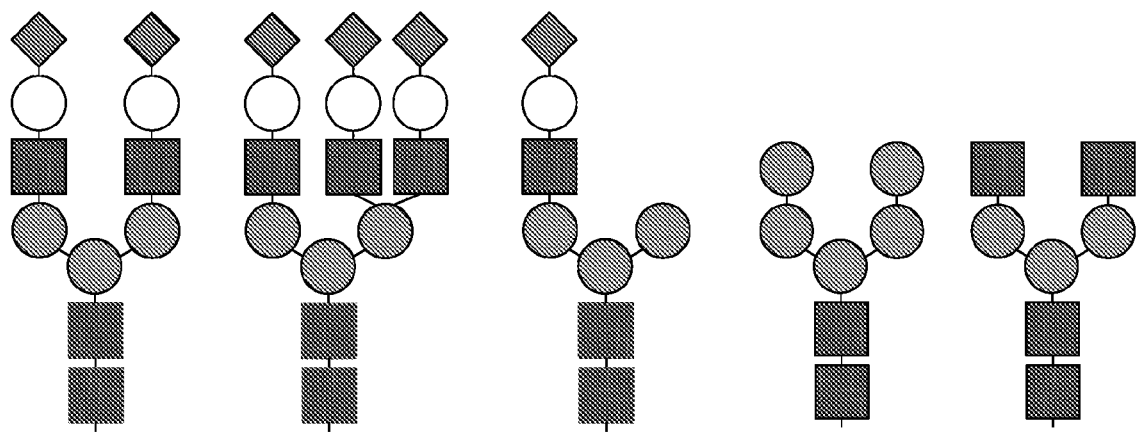

Transferrin (TF) is a secreted glycoprotein, having multiple glycoforms, containing glycans capped at their non-reducing ends with negatively charged sialic acid residues [11, 12]. TF plays a crucial role in homeostasis and transport of iron, as well as in protecting the body against free radical damage associated with unbound iron [13]. TF in serum is composed of 679 amino acid residues (~78 kDa MW) and has two glycosylation sites at asparagine $Asn_{432}$ and $Asn_{630}$ that are often occupied by N-linked glycans harboring various number of terminal (non-reducing end) sialic acid (or N-acetylneuraminic acid) residues, resulting in a heterogeneous populations of TF glycoforms [11, 14] (FIGS. 1A and 1B). TF in serum is exclusively comprised of fully sialylated glycoforms. In contrast, TF in CSF, referred to as β2-transferrin (β2TF), exists as a mixture of sialo (sTF) and asialoglycoforms (aTF) [7, 12] (FIGS. 1A and 1B). It has been speculated that the aTF in CSF originates from serum sTF through the action of brain neuraminidase [15]. Over the years, a number of methods have been designed to detect TF isoforms as biomarkers of CSF leakage, as well as various disorders of the central nervous system [16, 17]. Different separation methods relying on electrophoresis have been developed to separate TF isoforms, including isoelectric focusing [18], immunofixation gel electrophoresis [19], sodium dodecyl sulfate-polyacrylamide gel electrophoresis (SDS-PAGE) [20], and capillary electrophoresis (CE) [21].

The present invention encompasses a simple and rapid method enabling a spine surgeon to detect and/or measure CSF directly from a biological sample, such as a postoperative drainage. Spine surgeons can be faced with critical, time-sensitive decisions regarding patient care when a fluid leak is detected at the surgical site of a patient's postoperative incision. In some embodiments, the invention encompasses the use of chemical and/or enzymatic methods to specifically oxidize sTF in a biological sample, such as serum, allowing it to be conjugated to a hydrazide reagent (such as hydrazide magnetic microparticles) and selectively removed from the sample, allowing the rapid detection of CSF-derived aTF by a method amenable to use in rapid, real-time "dip-stick" analysis.

The biological sample can be any sample suspected of containing CSF, transferrin, and/or an asialo-transferrin. Exemplary biological samples include, for example, serum, blood, plasma, nasal fluid, aural fluid, a biopsy sample, a lymphatic fluid sample, fluid from a head or spinal wound or puncture, and fluid from a surgical incision site. In certain embodiments, the biological sample is serum. In additional embodiments, the biological sample is obtained from a subject, such as a human patient, during or after surgery. In yet additional embodiments, the biological sample is obtained from a surgical incision site or a post-operative fluid collection. The term "subject" is mean to encompass an animal subject including, but not limited, a human subject. In certain embodiments, the biological sample is obtained from a human subject or is of human origin.

The methods described herein encompass adding an oxidizing agent to the biological sample to generate oxidized sTF. The oxidizing agent is an oxidizing agent, such as a mild oxidizing agent, that can oxidize an alcohol group in TF to an aldehyde group. In some embodiments, the oxidizing agent is a chemical or enzymatic agent. In some embodiments, the oxidizing agent is one that oxidizes an alcohol group to an aldehyde in terminal residue of TF. A terminal residue is a monosaccharide residue at the non-reducing end of a transferrin molecule. In sialo-transferrin (sTF), a terminal residue is a sialic acid residue. Sialic acid residues can be removed from sTF, for example, by treatment with the enzyme neuraminidase. When the sialic acid groups are removed from sTF, the terminal monosaccharide residue is galactose. Exemplary oxidizing agents include, for example, periodates, such as periodate salts (for example, sodium periodate and potassium periodate). Oxidizing agents also include, for example, enzymes such as galactose oxidase.

An oxidized sTF is an sTF that is the product of an oxidation reaction, such as a mild oxidation reaction. In some embodiments, an oxidized sTF includes an aldehyde group, for example, in an oligosaccharide side chain of the TF. In some embodiments, the aldehyde group is in a terminal monosaccharide residue. A non-limiting example of an oxidized sTF is an sTF in which the C-7 position of a terminal sialic acid is an aldehyde group (see, for example, FIG. 1A). Another non-limiting example of an oxidized sTF is a sTF in which a terminal sialic acid residue has been removed and the C-6 position of a terminal galactose is an aldehyde group (see, for example, FIG. 5A).

A reagent comprising hydrazide groups includes, for example, any substance, compound or composition comprising hydrazide reactive groups. Reaction of carbonyl groups and hydrazide functional groups can form conjugates from the formation of hydrazone bonds. In some embodiments, the reagent comprising hydrazide reactive groups is a chemical reagent that includes hydrazide functional groups. In yet additional embodiments, the reagent comprising hydrazide groups is a solid support comprising hydrazide reactive groups. The support can be organic or inorganic, and includes, for example, beads, particles, films, membranes, tubes, wells, strips, rods, planar surfaces, for example, plate, paper-like, etc., fibers, and the like. Other examples of solid supports include for example, polymers, such as nitrocellulose and cellulose acetate. The hydrazide moieties can be ligated or otherwise chemically bound to any solid support. In some embodiments, the reagent comprising hydrazide reactive groups are particles. Preparation of hydrazide particles is described, for example, Hermanson 2013, Bioconjugate Techniques, $3^{rd}$ Edition, London, UK: Academic Press. Hydrazide particles are also commercially available. Hydrazide particles can be treated, coated or functionalized, such that the hydrazide reactive groups are present on the surface of the particles. In yet additional embodiments, the reagent is magnetic hydrazide particles, for example, magnetic hydrazide microparticles or nanoparticles (e.g., SiMAG hydrazide). In yet further embodiments, the reagent is a polymer support, such as nitrocellulose, that has been treated, coated, or functionalized such that hydrazide functional groups are present. In additional embodiments, the hydrazide reagent is a biotinylated hydrazide, such as (biotinyl hydrazide) and 6-(biotinamido)hexanehydrazide.

In some embodiments of the present invention, oxidized sTF in the biological sample is contacted with a reagent comprising hydrazide reactive groups to form a complex or conjugate, and the complex or conjugate is removed from the sample. The complex or conjugate can be removed from the sample by any appropriate means. For example, when the reagent comprising hydrazide reactive groups are particles, the particles can be removed from the sample using an appropriate method such as filtration, centrifugation, settling, and the like. In another example, when the reagent comprising hydrazide reactive groups are magnetic particles, the complex or conjugate can be removed using a magnetic separator. In yet an additional embodiment, when the hydrazide reagent is a biotinylated hydrazide, the biotinylated complex or conjugate can be captured using avidin-, streptavidin-, or other biotin-binding proteins. For example, the biotinylated complex can be captured using streptavidin-coupled detection techniques. In some embodiments, the biotinylated complex is captured using streptavidin-coated particles, for example, streptavidin-coated magnetic particles. Such particles include particles or beads to which streptavidin is covalently linked.

After removal of the complex or conjugate, the remaining sample (referred to herein as the "residual sample") has less sTF than that of the sample prior to conducting the oxidation and removal of sTF. For example, when magnetic hydrazide particles and a magnetic separator are used as described above, the supernatant comprises the residual transferrin. In some embodiments, the residual sample is substantially free of sTF, for example, the residual sample contains about 5% or less of the sTF that was originally present in the sample (prior to conducting the oxidation and removal of sTF). In yet other embodiments, the residual sample is free of sTF. The transferrin remaining in the residual sample is referred to as residual transferrin.

As discussed above, TF in CSF exists as a mixture of sialo (sTF) and asialo-transferrin (aTF). In contrast, in serum, the transferrin is exclusively comprised of fully sialylated glycoforms. Removal of sTF from the biological sample allows the detection and measurement of asialo-transferrin. Because asialo-transferrins are found in CSF (and not normally found in serum), detecting or measuring asialo-transferrin in the biological sample is indicative of a CSF leak. Residual transferrin or asialo-transferrin can be detected or measured, for example, using an anti-transferrin antibody. In some embodiments, the residual transferrin is detected or measured by immunoassay, for example, competitive immunoassay, sandwich immunoassay, lateral flow immunoassay, and/or ELISA. In some embodiments, the residual transferrin is detected or measured using labelled anti-transferrin antibody. As will be understood by those of skill in the art, the amount of transferrin or residual transferrin in the sample can be measured using standard curves.

In some aspects, an anti-transferrin antibody is a polyclonal antibody, a monoclonal antibody, or a transferrin-binding fragment of an antibody such as a Fab fragment. Anti-transferrin antibodies can be prepared using convention methods well known to skilled artisans such as methods set forth in Harlow, E., Using Antibodies: A Laboratory Manual, Cold Spring Harbor Laboratory Press, Cold Spring Harbor, N.Y., 1999, or can be purchased from a commercial supplier. In some embodiments, the methods and test strips described herein comprise the use of two antibodies (for example, an antibody in the binding region and an antibody in the capture region of a test strip). The two antibodies can be of different types, for example, the first antibody can be a mouse monoclonal antibody and the second antibody can be a rabbit polyclonal antibody, or vice versa, or the antibodies can bind to different epitopes of transferrin.

In additional embodiments, the residual transferrin is detected using ELISA wherein the residual sample is added to a solid support (for example, a multiwell plate) coated with an anti-transferrin antibody followed by the addition of a labelled detection antibody to the solid support. In some embodiments, the labelled detection antibody is a labelled anti-transferrin antibody. The labelled detection antibody can, for example, be an antibody conjugated to a detectable label including, for example, a fluorogenic label, a chromogenic label, a biotin molecule, and/or a gold particle. In certain aspects, the labelled detection antibody is a biotinylated antibody which can be detected by adding streptavidin-peroxidase complex, removing unbound conjugates, and adding a peroxidase substrate, such as TMB (3,3',5,5'-tetramethylbenzidine) or ABTS (2,2'-azino-bis(3-ethylbenzothiazoline-6-sulphonic acid)).

In yet additional aspects, the transferrin or residual transferrin is detected using a test strip. In some embodiments, the test strip comprises a sample loading region and binding region downstream of the sample loading region, wherein the binding region comprises an anti-transferrin antibody. In some aspects, the anti-transferrin antibody in the binding region is a labeled antibody. Transferrin is detected and/or measured as the labelled anti-transferrin antibody become visible or is otherwise detected. In additional aspects, the test strip further comprises a capture region downstream of the binding region, wherein the capture region comprises a capture reagent that binds the anti-transferrin antibody-transferrin complex. In yet additional embodiments, the capture reagent is immobilized in the test strip. In further aspects, the capture reagent is an antibody. In yet further embodiments, the test strip additionally comprises a control region comprising a control reagent. A control reagent can, for example, be an antibody with binding affinity for the labelled antibody.

As discussed above, the invention also encompasses a method of detecting a CSF leak in a subject during or after surgery comprising: a. obtaining a first biological sample from the subject prior to surgery and measuring the transferrin present in the first sample; and b. obtaining a second biological sample from the subject during or after surgery and measuring the transferrin present in the second sample; wherein a higher amount of transferrin present in the second sample compared to the transferrin present in the first sample indicates a CSF leak. In some aspects, the transferrin is detected by immunoassay, for example, as described above. In yet additional embodiments, the transferrin is detected using a test strip. In certain aspects, the sample is diluted after it is obtained. In yet further aspects, sTF is removed from the first sample and from the second sample before the transferrin is measured.

As described above, the invention also encompasses a test strip for detecting or measuring transferrin in a sample comprising a. a sample loading region; b. a filtration region downstream of the sample loading region, wherein the filtration region comprises an immobilized reagent that binds to sTF; and c. a binding region downstream of the filtration region comprising an anti-transferrin antibody. In some embodiments, the test strip additionally comprises a control region comprising a control reagent, for example, a control reagent antibody. As discussed above, in some embodiments, the control reagent is an antibody with binding affinity for the labelled antibody and for labelled antibody complexes, for example, if the labelled antibody is a rabbit antibody, the control antibody can be a goat anti-rabbit antibody. In yet additional aspects, the test strip further comprises a capture region downstream of the binding region and wherein the capture region comprises a capture reagent that binds the anti-transferrin antibody-transferrin complex; for example, the capture reagent is an anti-transferrin antibody. In certain aspects, the capture reagent is immobilized on the test strip. In further embodiments, the anti-transferrin antibody in the binding region is labelled.

In certain aspects, the immobilized reagent that binds to sTF on the test strip is a reagent that binds to oxidized sTF, and wherein the oxidized sTF comprises an aldehyde group in a terminal residue of the sTF. In some embodiments, the reagent, for example, comprises hydrazide reactive groups. In yet further embodiments, the filtration region comprises a nitrocellulose, PVDF, or other membrane. In additional embodiments, the membrane comprises hydrazide reactive groups, for example, a nitrocellulose membrane can be coated or functionalized such that hydrazide reactive groups are present and preferably, immobilized. In yet additional embodiments, the filtration region comprises hydrazide particles as described herein wherein the particles are immobilized in the filtration region. sTF in the biological sample can thus be retained in the filtration region of the test strip and the residual transferrin can move through the test strip by lateral flow.

Lateral flow and lateral flow test strips are well-known in the art. In exemplary methods, a test sample is added to the test surface, typically followed by a chase buffer. The chase buffer facilitates the flow of fluids across the test surface. The test strip also contains labelled antibodies, such as gold particles attached to antibodies. The analyte present in the sample (transferrin or residual transferrin) can bind to the labeled antibodies and the complex migrates through the membrane by capillary action. The analyte and label complex can then bind to antibodies which are immobilized on the membrane, creating a detectable indicator, such as a colored line, in the test zone. If no analyte is present in the sample, then the conjugate migrates past the test zone and will not bind to the antibodies on the test line of the membrane. Optionally, a control reagent can capture and bind excess conjugate. In some embodiments, a control reagent and line produced therefrom is a control that indicates the test was run properly. In some embodiments, the results can be read in about 1 to about 60 minutes, or in about 1 minute to about 30 minutes, or in about 5 to about 15 minutes.

In yet additional embodiments, the invention is a device for detecting the presence of transferrin in a sample, wherein the device comprises a test strip described herein and a housing containing the test strip, wherein the housing comprises at least one opening to expose the surface of the test strip in the sample loading zone to the sample. In some embodiments, the device is a handheld device.

In yet additional aspects, the invention encompasses a kit comprising the test strip or device described herein, and a container containing an oxidizing agent. In some embodiments, the oxidizing agent is sodium or potassium periodate. In yet additional embodiments, the oxidizing agent is galactose oxidase.

Various embodiments described herein involve the use of labelled antibodies. Exemplary labels include, for example, enzymes and their resultant effects on a substrate, colloidal metal particles, latex with dye incorporated, and dye particles. An enzyme can react on a substrate to produce a product that is detectable, for example, by color of absorption (e.g., ultraviolet, visible, infrared), or by fluorescence, in yet additional embodiments, the label is a fluorogenic label, a chromogenic label, a biotin molecule, and/or a metal particle. In some aspects, the metal particles can comprise platinum, gold, silver, selenium, or copper or any other of metal compounds which exhibit characteristic colors. The metal particles suitable for use in the present invention can be prepared by conventional methodologies. For example, the preparation of gold sol particles is described Frens, *Nature* 241: 20-22 (1973).

In further embodiments, the test strip comprises a solid support (plastic, cardboard, or other rigid or semi-rigid material, and a membrane on top of the solid support (in some examples, the membrane is a nitrocellulose or PVDF membrane). The membrane includes the sample loading region and binding region as described herein. The membrane can also include the capture region and/or control region.

The invention also encompasses a method of detecting a transferrin or measuring the amount of transferrin in a biological sample comprising contacting the sample with a test strip, device, or kit described herein, wherein the method comprises detecting or measuring the transferrin in the binding region or capture region or downstream of the binding region or capture region. In some embodiments, the transferrin is β2-transferrin, for example, asialo-transferrin. In certain aspects, the sample is a biological sample. In yet additional embodiments, the invention is a method of detecting the presence of CSF in biological sample comprising contacting the sample with a test strip, device or kit described herein, wherein the method comprises detecting or measuring the transferrin in the binding region or capture region or downstream of the binding region or capture region.

The invention is illustrated by the following examples which are not meant to be limiting in any way.

EXEMPLIFICATION

2. Materials and Methods
2.1 Enzyme Reactions and Labeling

Human serum sTF (10 mg/mL, Sigma) was dissolved in 1× Glycobuffer (20 mM sodium acetate buffer at pH 5.5, including 5 mM $CaCl_2$)). The human sTF solution was treated with neuraminidase (1 mg/mL in 1× Glycobuffer, Sigma) at 37° C. overnight to generate aTF. Both sTF and aTF were labeled with NHS-rhodamine (Pierce) following the manufacturer's protocol. All unreacted rhodamine was removed by column chromatography on a PD MiniTrap G-25 column (GE Heathcare).

A two-step enzymatic reaction including neuraminidase (Sigma) and galactose oxidase (Sigma) was performed on human CSF (PrecisionMed), on pooled human serum (Innovative Research Inc.) and on individual human serum samples (BioreclaimationIVT). Both CSF and serum were first diluted 2-fold and 200-fold, respectively, in 1× Glycobuffer. Diluted CSF (10 µL) and diluted serum (10 µL) were each treated for 1 h with neuraminidase (10 µL of 1 mg/mL) at 37° C., followed by treatment for varying times with galactose oxidase, dissolved in 100 mM, pH 7.2, Tris buffer (10 µL of 0.5 KU/mL) at 37° C.

2.2 Agarose Gel Electrophoresis

After dissolving 0.4 g of agarose powder (Sigma) in 40 mL of 1× Tris-borate buffer (89 mM Tris base and 89 mM boric acid, pH 8.0), agarose gel (1%) was prepared by melting the agarose in a microwave oven and then the melted agarose solution was poured into the casting tray, forming a solid gel after cooling at room temperature. Loading samples were prepared by mixing the rhodamine-labeled proteins (20-320 ng in 10 µL) with 30% glycerol (2 µL). After loading the protein samples, the gel was subjected to electrophoresis at 200 V for 15 min.

2.3 Periodate Oxidation

Mild periodate oxidation was performed with 1 mM $NaIO_4$ at 4° C. (on ice) for 30 min, to oxidize the non-reducing end sialic acid residues in TF. Excess periodate and formaldehyde, generated during periodate oxidation, were removed by PD Mini Trap G-25 column (GE Heathcare). After desalting and buffer exchange with 100 mM, pH 7.0, sodium phosphate buffer using a G-25 column, the TF containing oxidized sialic acid residues were captured with SiMAG-Hydrazide microparticles (Chemicell).

2.4 Coupling and Separation of Sialo-Proteins

After washing SiMAG-Hydrazide particles (10 mg/ml) two-times with pH 7.0, 100 mM sodium phosphate buffer, the particles were incubated with TF containing oxidized sialic acid residues for 3 h at 20° C. The protein-particle conjugates were pelleted using a magnetic separator. Proteins remaining in the supernatant were collected and concentrated with Amicon ultracentrifugal filters (Ultracel-3K). The concentrated samples containing aTF were analyzed by agarose gel electrophoresis or using a transferrin ELISA kit (Abcam).

2.5 ELISA Assay

Human TF in test samples could be detected with transferrin ELISA assay kit (Abcam). Briefly, standards or test samples were added to the 96-well plates pre-coated with TF specific antibody, then specific biotinylated TF detection antibody was added, and the plates were washed with wash buffer. Streptavidin-peroxidase complex was added and unbound conjugates were washed away with wash buffer. TMB was used to visualize streptavidin-peroxidase enzymatic reaction as TMB is catalyzed by peroxidase to produce a blue color product that changes into yellow after adding acidic stop solution. The absorbance of yellow color was immediately measured with a microplate reader (SpectraMax M5, Molecular Devices) at a wavelength of 450 nm. The detailed ELISA protocols were followed by manufacture's guideline (Abcam).

3. Results and Discussion

Figure 2A:
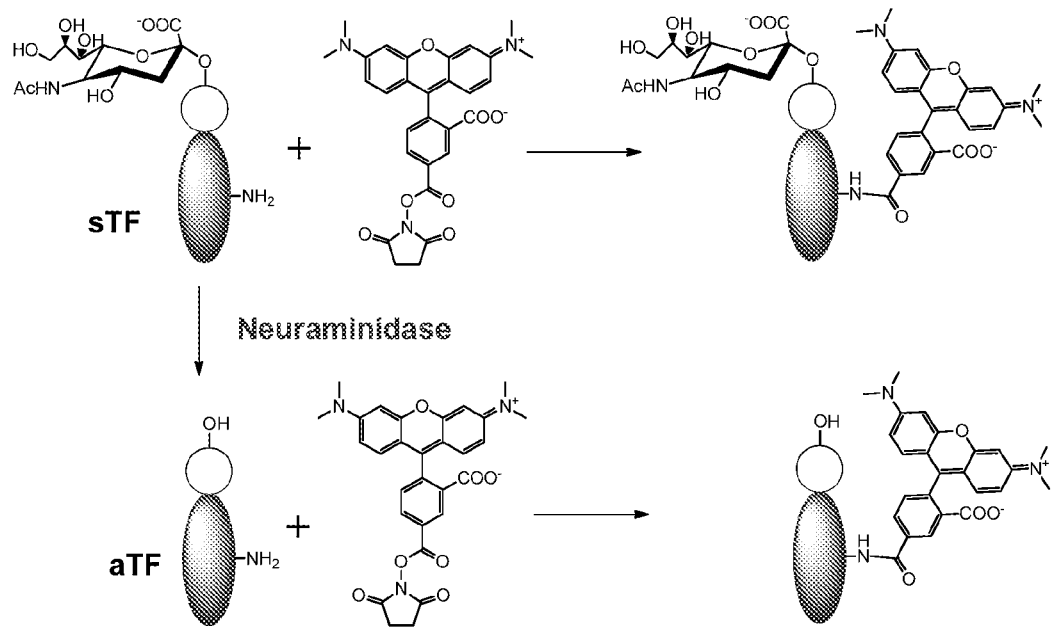
FIGS. 2A, 2B and 2C show an electrophoresis-based assay for determination of TF glycoforms.
Figure 2B:
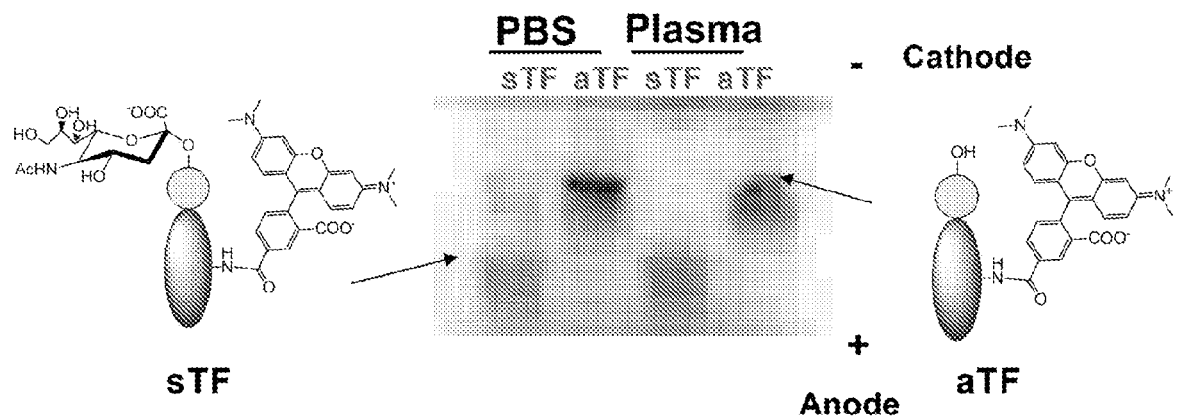
Figure 2C:
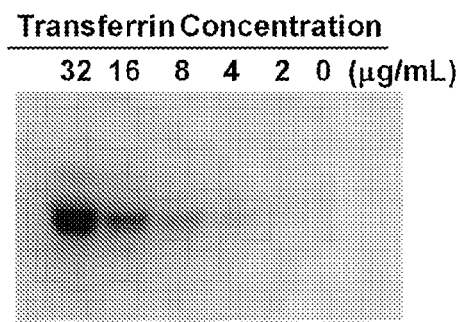

Neuraminidase was used to generate aTF from sTF. After removal of sialic acid residues, TF was labeled using NHS-rhodamine (FIG. 2A). Rhodamine-labeled aTF and sTF could be separated using agarose gel electrophoresis (FIG. 2B). The results showed that more negatively charged sTF migrated closer to the anode. In addition, rhodamine-labeled transferrin could be selectively detected in human plasma (FIG. 2B). The detection limit for rhodamine-labeled TF was 2 µg/mL (FIG. 2C), which is similar to detection by immunofixation (IFE) gel electrophoresis [19].

Figure 3A:
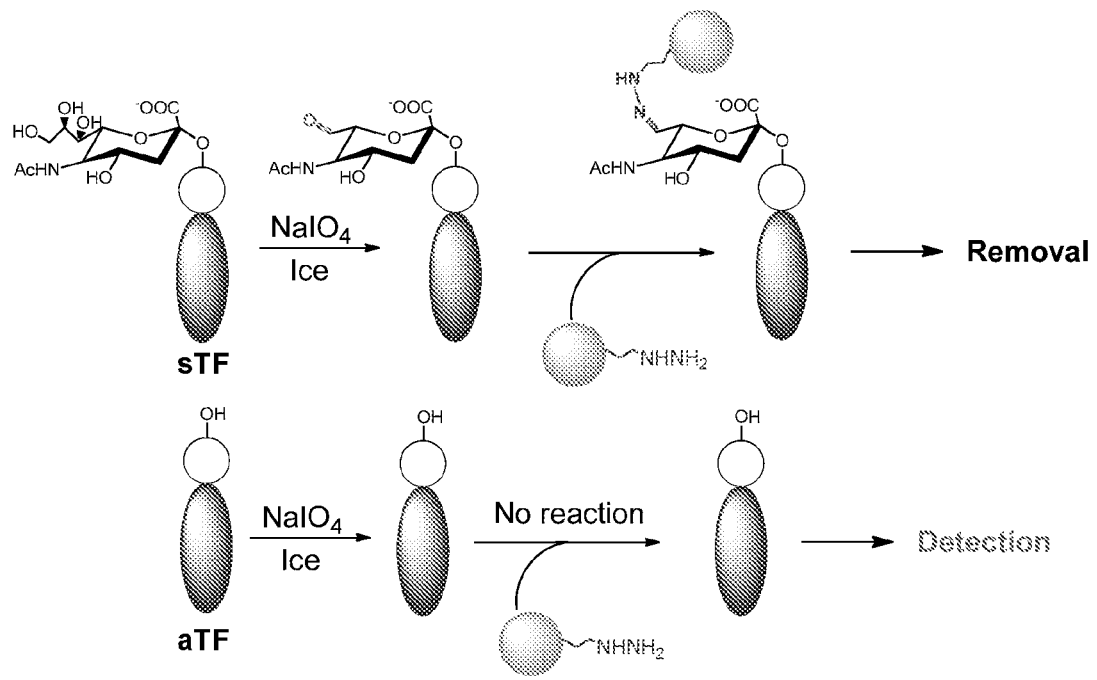
FIGS. 3A and 3B shows the single-step periodate glycan oxidation for the separation of TF glycoforms from buffer glycan.
Figure 3B:
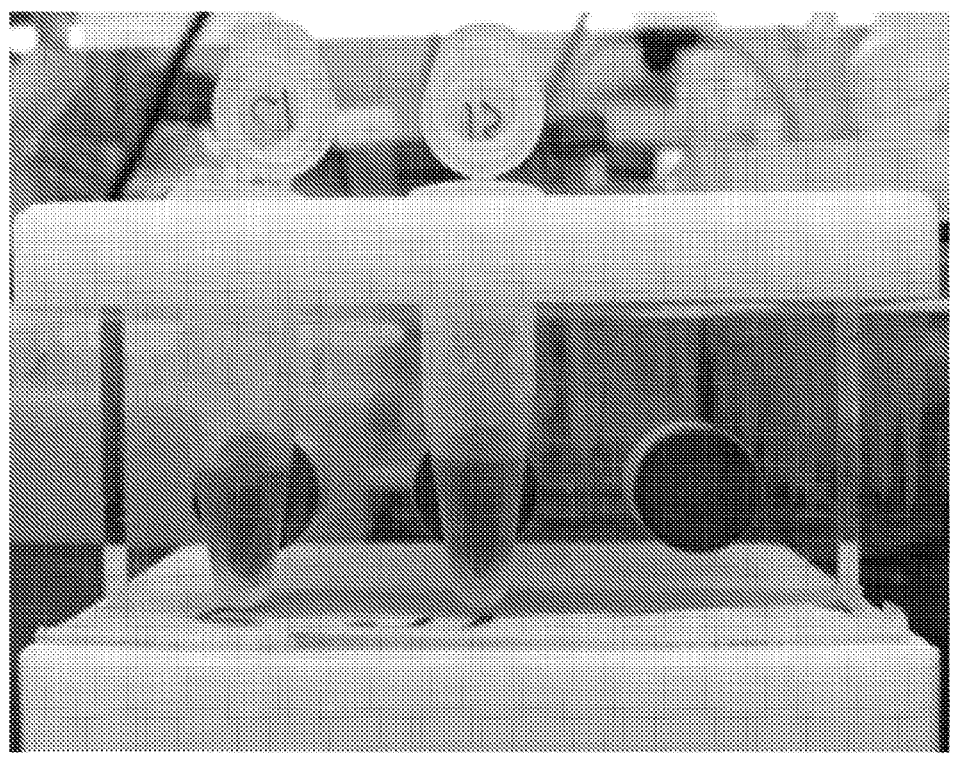
Figure 3C:
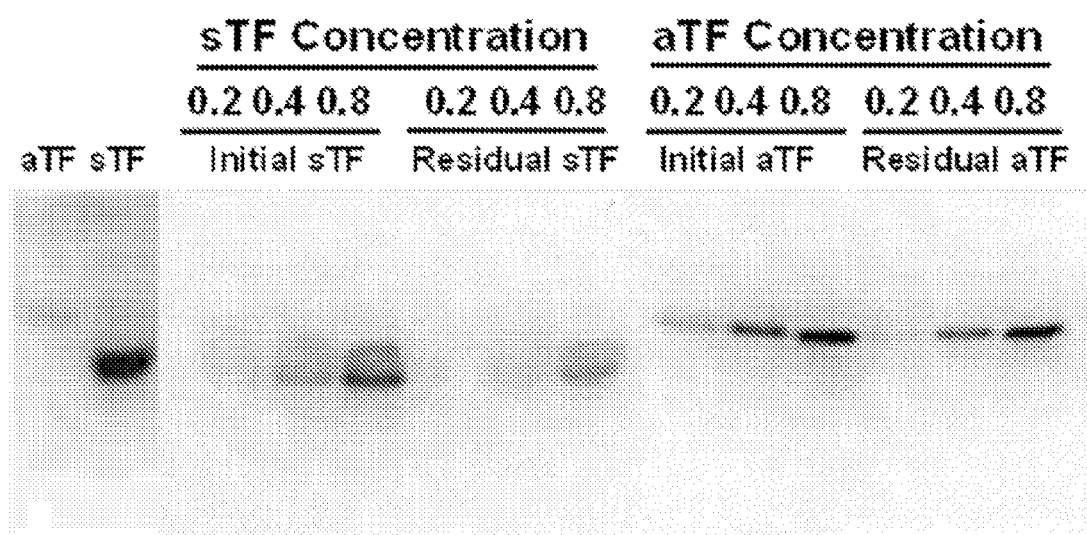
FIG. 3C shows the separation and detection of aTF and trace sTF in buffer by electrophoresis.

Because human serum TF is a glycoprotein with two glycans containing non-reducing terminal sialic acid residues (sTF) and CSF contains both sTF and aTF [7, 12], mild periodate oxidation [22] renders sTF capturable as a hydrazone (FIG. 3A). Thus, we selectively removed sTF to facilitate the detection of aTF in CSF (FIG. 3A). The terminal sialic acid residues in sTF were oxidized to their aldehyde derivatives by mild treatment with sodium periodate [22, 23], and the oxidized sTF was captured by its covalent coupling to SiMAG-Hydrazide (magnetic hydrazide microparticles) in the form of a stable hydrazone linkage. The sTF-beads conjugate could then be easily removed using a magnetic separator (FIG. 3B). As a proof of concept, we subjected different concentrations (100 µL) of sTF and aTF to mild periodate oxidation (1 mM $NaIO_4$ at 4° C. for 30 min), selectively introducing an aldehyde at the C-7 position of the terminal sialic acid residues in sTF. After removing unreacted oxidation reagent by desalting on a Sephadex G-25 column, the aldehyde group-containing sTF was captured by incubating with 200 µL of SiMAG-Hydrazide (10 mg/mL) at 20° C. for 3 h. The captured sTF was removed with a magnetic separator and the supernatant, containing aTF with trace amounts residual sTF was assayed using agarose gel electrophoresis (FIG. 3C). The results showed that sTF was selectively removed through covalent capture with SiMAG-Hydrazide and that the aTF remained in supernatant buffer. At high concentrations of sTF (0.8 mg/mL), ~50% of sTF remained in supernatant buffer because of the presence of insufficient amounts of SiMAG-Hydrazide, required for its capture. When we doubled the amount of SiMAG-Hydrazide (20 mg/mL), the residual sTF remaining dropped to <3% (data not shown). This mild periodate oxidation quickly and selectively introduces aldehyde groups into sTF within 30 min (FIG. 3C) and coupling with SiMAG-Hydrazide magnetic microparticles can be accomplished in 3 h requiring an overall pre-treatment time of <5 h. Encouraged by these results, we applied the protocol developed to detect CSF aTF in samples consisting of mixtures of CSF and serum.

Figure 4A:
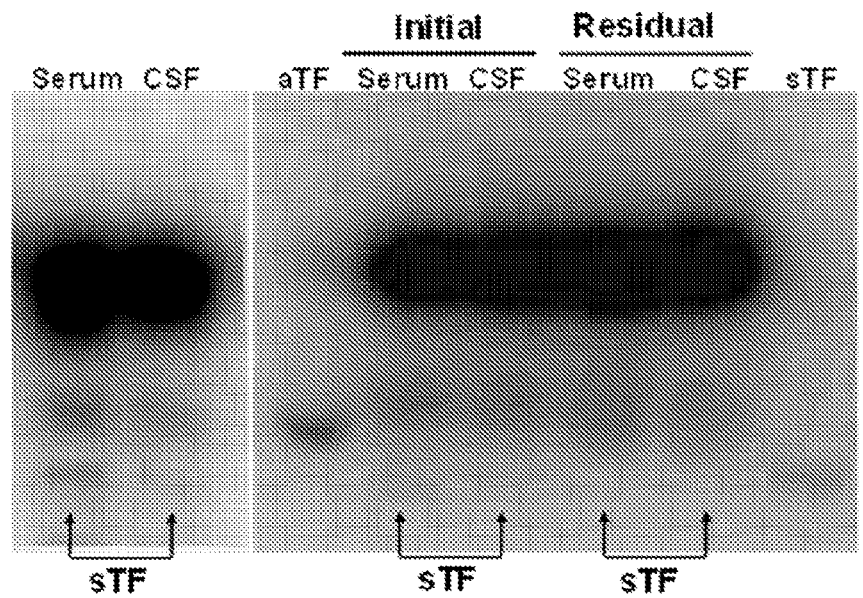
FIGS. 4A, 4B, 4C and 4D show separation of sTF from TF glycoforms using single-step periodate oxidation in a mixture of CSF and serum.

Mixtures (10 µL) of rhodamine-labeled (200-fold) diluted serum and rhodamine-labeled (2-fold) diluted CSF were subjected to mild periodate oxidation as a proof-of-concept test on a sample containing both CSF and serum. After selective separation of sTF from both serum and CSF following the protocol described above, residual sTF in agarose gel was analyzed (FIG. 4A). The level of sTF in serum was higher than the sTF in CSF and all the sTF present in both serum and CSF was successfully removed (bottom bands in FIG. 4A) by mild periodate oxidation and capture with SiMAG-Hydrazide.

Figure 4B:
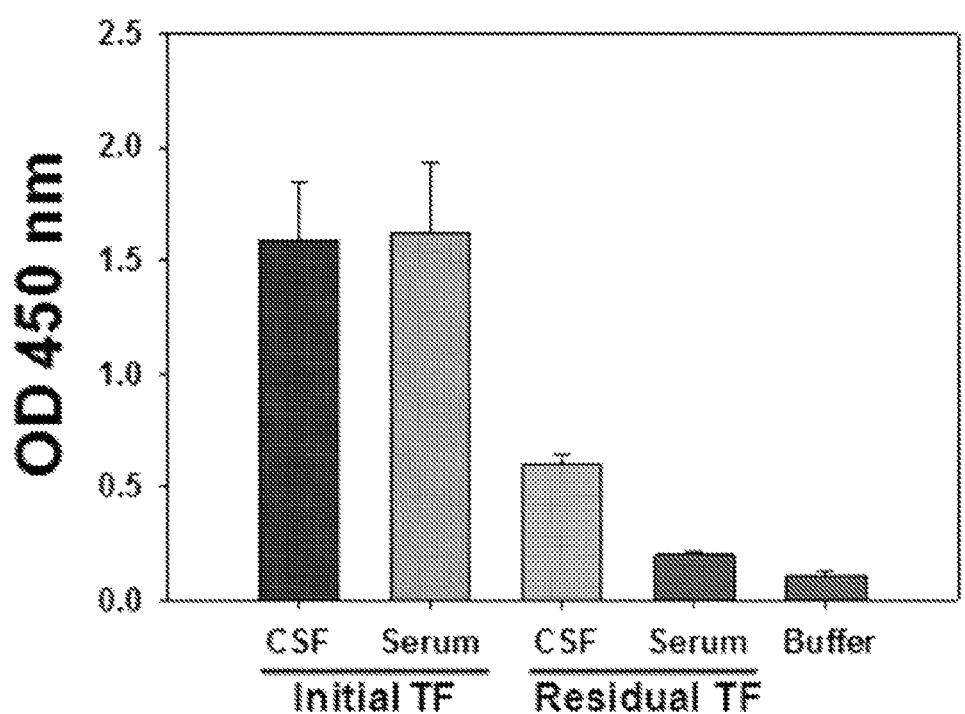
Figure 4C:
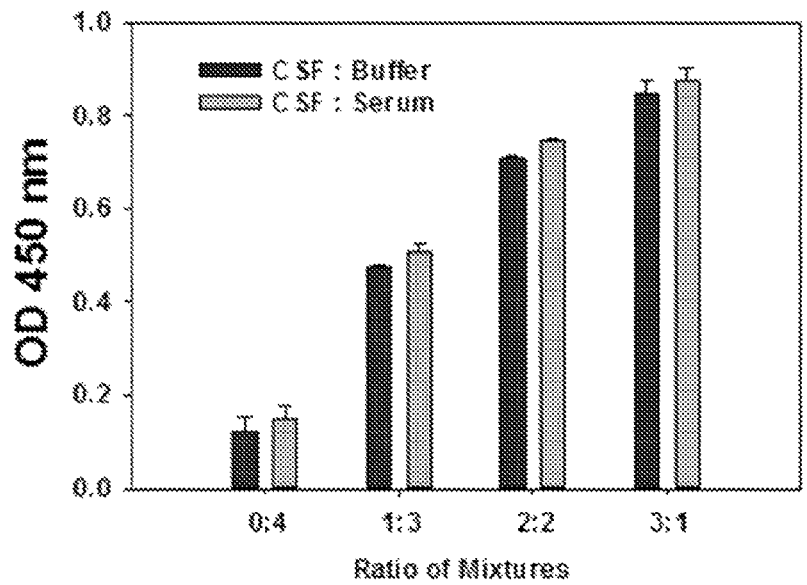
Figure 4D:
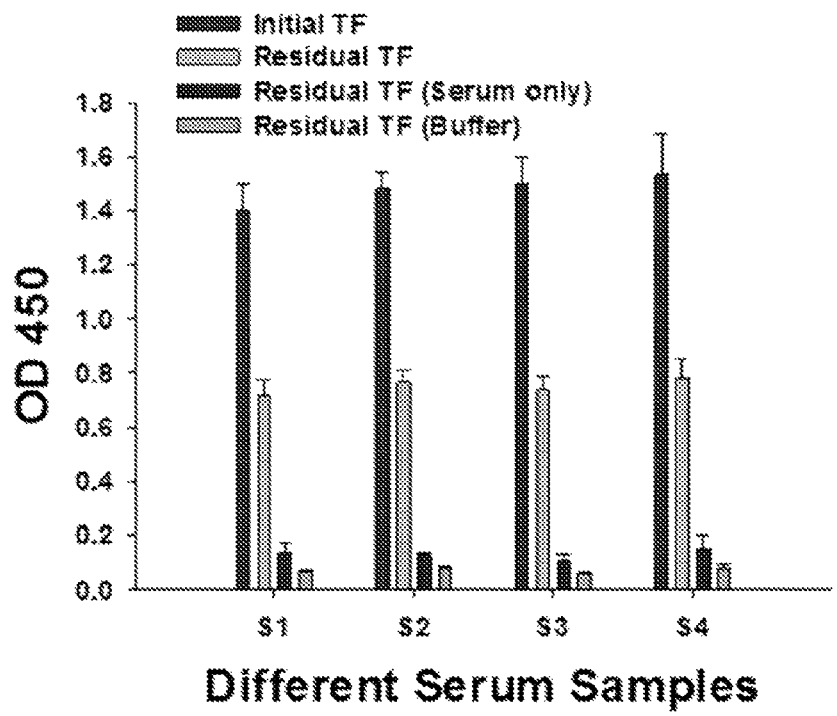

It was not possible to detect directly aTF bands in agarose gel because of the complex mixture of proteins present in both serum and CSF. Human transferrin ELISA, therefore, was performed to specifically capture only TF in order to detect the residual TF in both CSF and serum (FIG. 4B). The amount of residual TF (aTF) in CSF was clearly higher than that of the residual TF (uncaptured sTF) in serum. However, trace amount of residual TF (uncaptured sTF) was still present in serum either because of incomplete oxidation of sialic acid residues or inefficient capture. Based on standard curve of TF in ELISA (data not shown), the level of residual trace TF in serum was ~7 ng/mL, similar to that of the buffer control. In contrast, residual TF (aTF) in CSF was ~60 ng/mL corresponding to one-third of the initial amount of TF in CSF (~170 ng/mL). This result was expected as only ~30% of the total TF in CSF is aTF [7]. We prepared mixtures of serum and CSF with different volume ratio to simulate real situation of CSF leakage. After selective removal of sTF from the mixtures of serum and CSF with the above protocols, residual TF (mainly aTF) was measured by ELISA kit (FIG. 4C). The results showed that the amounts of the residual TFs from the mixtures of serum and CSF were similar to those of the residual TF from different amounts of CSF in buffer, which is the same dilution of the mixtures of serum and CSF. In addition, we used multiple serum samples (S1: age 29/African male, S2: age 41/Caucasian male, S3: age 61/Hispanic female, S4: age 21/African female) and prepared the mixture (1:1 v/v ratio) of CSF and various serums and removed sTF selectively. Both the initial and residual TFs from the mixtures of different serum samples and CSF were measured by ELISA kit (FIG. 4D). The residual TF (mainly aTF) from CSF were clearly detected regardless of type of serum and the amounts of residual TF from serum were similar to negative control (only buffer).

Figure 5A:
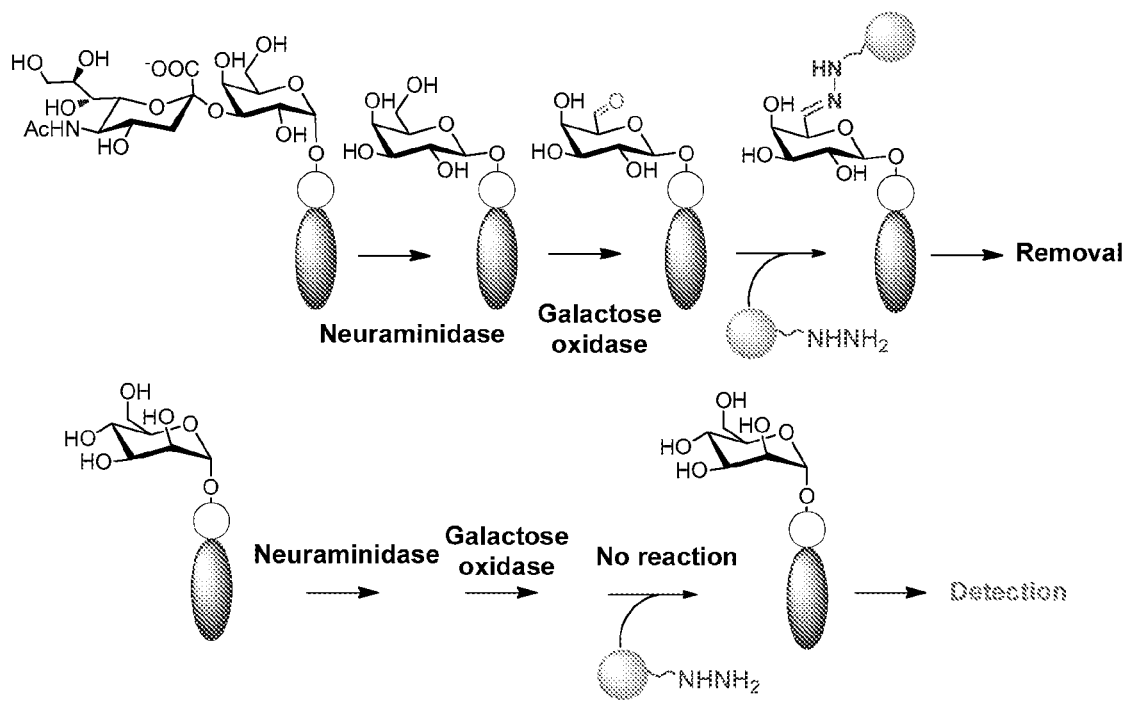
FIGS. 5A and 5B shows the two-step enzymatic oxidation for the separation of TF glycoforms.
Figure 5B:
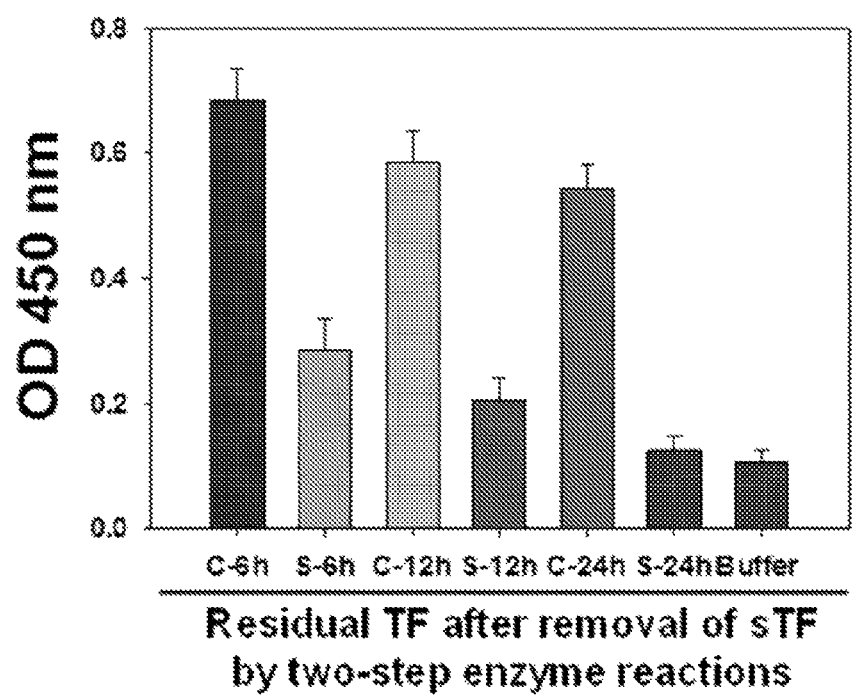

Although we could discriminate between CSF and serum through the selective removal of sTF, the complete removal of serum sTF is desirable for the accurate determination of aTF in CSF when analyzing mixtures of CSF and serum. Hence, we examined a two-step enzymatic (neuraminidase and galactose oxidase) reaction for generating aldehyde groups in sTF since enzymes show very high substrate specificity. Because there are neither non-reducing terminal sialic acid residues nor galactose residues in CSF-derived aTF [7], a two-step enzymatic reaction should be quantitative and selectively introduce aldehyde groups at the C-6 position of the galactose residue into sTF (FIG. 5A). A 10-μL sample of both diluted (2-fold) CSF and (200-fold) serum was added to neuraminidase (10 μL of 1 mg/mL) and galactose oxidase (10 μL of 0.5 KU/mL) at 37° C. After subjecting the samples with two enzymes for different lengths of time, SiMAG-Hydrazide (100 μL of 10 mg/mL) was added to the reaction mixture and incubated for an additional 3 h at 20° C. to capture the oxidized sTF. After pulling down the microparticle-captured oxidized sTF with a magnetic separator, residual TF in the supernatant was determined with ELISA (FIG. 5B). The results showed that we could completely remove serum sTF in this two-step enzymatic reaction, although this procedure required 24 h. However, although this two-step process could successfully remove all the sTF, this pre-treatment step required ~24 h, too long to accommodate a surgeon's immediate clinical decision. Consequently, future work will be aimed at improving the selectivity of periodate pretreatment, as well as decreasing the time required for the two-step enzymatic pretreatment.

Rapid and sensitive detection of CSF is crucial [24] to make real-time critical decisions regarding patient care. For example, if a CSF leakage occurs post surgery, a patient may need to quickly return to the operating room to explore and repair the CSF leak, which would in turn treat the positional headaches and potential infection from contact with contaminated skin, thereby increasing the risk of developing meningitis. At the time fluid is first noticed, and if the surgeon is unsure whether the fluid contains CSF, the surgeon can often only wait for confirmatory analysis, which delays action and can lead to poorer patient prognosis. In some cases a patient might not a classic presentation of a positional headache, which can further delay the diagnosis of a CSF fluid leak. Thus, a rapid test that can detect the presence of CSF fluid would allow spine surgeons to make immediate clinical decisions leading to improved patient outcomes.

The formation of β2 transferrin (β2TF) is mediated by neuraminidase activity within the central nervous system [25]. Therefore, β2TF represent a potential highly selective marker protein for CSF leakage, since it is only located within the CSF where it is present as asialylated TF glycoforms, aTF. This anatomical selectivity enabled the development of a pre-treatment method for rapid and selective removal of serum sTF in fluid leak samples, which would enable detection of CSF-associated β2TF (aTF). A rapid pre-treatment method would also facilitate the commercial development of an easy to use a simple TF test kit.

REFERENCES

[1] Barrios, C., Ahmed, M., Arrotegui, J. I., Bjornsson, A., *J Spinal Disorders* 1990, 3, 205-209.
[2] Cammisa, F. P., Jr., Girardi, F. P., Sangani, P. K., Parvataneni, H. K., Cadag, S., Sandhu, H. S., *Spine* 2000, 25, 2663-2667.
[3] Khan, M. H., Rihn, J., Steele, G., Davis, R., Donaldson, W. F., 3rd, Kang, J. D., Lee, J. Y., *Spine* 2006, 31, 2609-2613.
[4] Stolke, D., Sollmann, W. P., Seifert, V., *Spine* 1989, 14, 56-59.
[5] Wang, J. C., Bohlman, H. H., Riew, K. D., *J Bone Joint Surgery (Am)* 1998, 80, 1728-1732.
[6] Eismont, F. J., Wiesel, S. W., Rothman, R. H., *J Bone Joint Surgery (Am)* 1981, 63, 1132-1136.
[7] Brown, K. J., Vanderver, A., Hoffman, E. P., Schiffmann, R., Hathout, Y., *Int J Mass Spectrom* 2012, 312, 97-106.
[8] Jou, Y. J., Lin, C. D., Lai, C. H., Chen, C. H., Kao, J. Y., Chen, S. Y., Tsai, M. H., Huang, S. H., Lin, C. W., *Anal Chim Acta* 2010, 681, 41-48.
[9] Whitfield, J. B., *Clin Chem* 2002, 48, 2095-2096.
[10] Wang, C., Li, C., Gong, W., Lou, T., *Biomark Res* 2013, 1, 9.
[11] Coddeville, B., Carchon, H., Jaeken, J., Briand, G., Spik, G., *Glycoconj J* 1998, 15, 265-273.
[12] de Jong, G., van Noort, W. L., van Eijk, H. G., *Electrophoresis* 1992, 13, 225-228.
[13] Kallee, E., Lohss, F., Debiasi, S., *Nucl Med* 1963, 2, Suppl 1:111-118.
[14] Iourin, O., Mattu, T. S., Mian, N., Keir, G., Winchester, B., Dwek, R. A., Rudd, P. M., *Glycoconj J l* 1996, 13, 1031-1042.
[15] Nandapalan, V., Watson, I. D., Swift, A. C., *Clinical otolaryngology and allied sciences* 1996, 21, 259-264.
[16] Arrer, E., Meco, C., Oberascher, G., Piotrowski, W., Albegger, K., Patsch, W., *Clin Chem* 2002, 48, 939-941.
[17] Vanderver, A., Schiffmann, R., Timmons, M., Kellersberger, K. A., Fabris, D., Hoffman, E. P., Maletkovic, J., Hathout, Y., *Clin Chem* 2005, 51, 2031-2042.
[18] Roelandse, F. W., van der Zwart, N., Didden, J. H., van Loon, J., Souverijn, J. H., *Clin Chem* 1998, 44, 351-353.
[19] Normansell, D. E., Stacy, E. K., Booker, C. F., Butler, T. Z., *Clin Otolaryngol Allied Sci* 1994, 1, 68-70.
[20] Gorogh, T., Rudolph, P., Meyer, J. E., Werner, J. A., Lippert, B. M., Maune, S., *Clin Chem* 2005, 51, 1704-1710.

[21] Legros, F. J., Nuyens, V., Baudoux, M., Zouaoui Boudjeltia, K., Ruelle, J. L., Colicis, J., Cantraine, F., Henry, J. P., *Clin Chem* 2003, 49, 440-449.
[22] Zeng, Y., Ramya, T. N., Dirksen, A., Dawson, P. E., Paulson, J. C., *Nat Methods* 2009, 6, 207-209.
[23] De Bank, P. A., Kellam, B., Kendall, D. A., Shakesheff, K. M., *Biotechnol Bioeng* 2003, 81, 800-808.
[24] Choi, D., Spann, R., *Br J Neurosurg* 1996, 10, 571-575.
[25] Gallo, P., Bracco, F., Morara, S., Battistin, L., Tavolato, B., *J Neurol Sci* 1985, 70, 81-92.

While this invention has been particularly shown and described with references to preferred embodiments thereof, it will be understood by those skilled in the art that various changes in form and details may be made therein without departing from the scope of the invention encompassed by the appended claims.

What is claimed is:

1. A test strip for detecting or measuring asialo-transferrin in a sample comprising:
   a. a sample loading region;
   b. a filtration region downstream of the sample loading region, wherein the filtration region comprises an immobilized first reagent that binds to oxidized sialo-transferrin (sTF); and
   c. a binding region downstream of the filtration region comprising an anti-transferrin antibody, wherein the immobilized first reagent that binds to oxidized sTF comprises reactive hydrazide groups on particles, and wherein the oxidized sTF comprise aldehyde groups in terminal sialic acid residues of the sTF.

2. The test strip of claim 1, further comprising a control region comprising a control antibody.

3. The test strip of any of claim 1, further comprising a capture region downstream of the binding region, wherein the capture region comprises an immobilized capture reagent that binds an anti-transferrin antibody-transferrin complex.

4. The test strip of claim 3, wherein the capture reagent is an anti-transferrin antibody.

5. The test strip of claim 1, wherein the anti-transferrin antibody in the binding region is detectably-labeled.

6. The test strip of claim 5, wherein the anti-transferrin antibody is conjugated to a fluorogenic label, a chromogenic label, a biotin molecule, and/or a gold particle.

7. A device for detecting the presence of transferrin in a sample, wherein the device comprises:
   a. the test strip of claim 1;
   b. a housing containing the test strip, wherein the housing comprises at least one opening to expose the surface of the test strip in the sample loading zone to the sample.

8. A kit comprising the test strip of claim 1, and a container containing an oxidizing agent, and a sample of human serum.

9. The kit of claim 8, wherein the oxidizing agent is a periodate salt.

10. A method of detecting the presence of asialo-transferrin in, or measuring the amount of asialo-transferrin in, a biological sample comprising contacting the sample with a test strip of claim 1, and detecting or measuring transferrin bound in the binding region or downstream of the capture region.

11. The method of claim 10, wherein the sample is a serum sample.

* * * * *